(12) United States Patent
Studer et al.

(10) Patent No.: US 8,784,103 B2
(45) Date of Patent: Jul. 22, 2014

(54) CONNECTION ARRANGEMENT BETWEEN A DENTAL IMPLANT AND AN ABUTMENT

(75) Inventors: Roger Studer, Binningen (CH); David Egli, Basel (CH); Ulrich Mundwiler, Tenniken (CH)

(73) Assignee: Straumann Holding AG, Basel (CH)

( * ) Notice: Subject to any disclaimer, the term of this patent is extended or adjusted under 35 U.S.C. 154(b) by 507 days.

(21) Appl. No.: 12/678,618

(22) PCT Filed: Sep. 16, 2008

(86) PCT No.: PCT/EP2008/062312
§ 371 (c)(1),
(2), (4) Date: Mar. 17, 2010

(87) PCT Pub. No.: WO2009/037260
PCT Pub. Date: Mar. 26, 2009

(65) Prior Publication Data
US 2010/0203476 A1    Aug. 12, 2010

(30) Foreign Application Priority Data
Sep. 17, 2007    (EP) ..................................... 07116564

(51) Int. Cl.
*A61C 8/00* (2006.01)
(52) U.S. Cl.
USPC ........................................................ 433/172
(58) Field of Classification Search
USPC ........................ 433/172–176, 201.1; 81/10; 606/300–331, 269, 270, 274; 411/999
See application file for complete search history.

(56) References Cited

U.S. PATENT DOCUMENTS

| | | | |
|---|---|---|---|
| 4,713,003 A * | 12/1987 | Symington et al. | 433/173 |
| 5,372,598 A * | 12/1994 | Luhr et al. | 606/285 |
| 5,443,467 A * | 8/1995 | Biedermann et al. | 606/65 |
| 5,571,016 A | 11/1996 | Ingber et al. | |
| 5,660,545 A | 8/1997 | Bailey et al. | |
| 5,695,335 A | 12/1997 | Haas et al. | |
| 5,733,122 A * | 3/1998 | Gordon | 433/172 |
| 5,947,733 A | 9/1999 | Sutter et al. | |
| 6,030,389 A * | 2/2000 | Wagner et al. | 606/71 |
| 6,224,598 B1 * | 5/2001 | Jackson | 606/305 |
| 6,447,295 B1 | 9/2002 | Kumar et al. | |
| 6,663,388 B1 * | 12/2003 | Schar et al. | 433/173 |

(Continued)

FOREIGN PATENT DOCUMENTS

| | | |
|---|---|---|
| CN | 1460010 A | 9/2012 |
| DE | 92 02 656 U1 | 4/1992 |

(Continued)

OTHER PUBLICATIONS

International Search Report dated Jan. 28, 2009.

(Continued)

*Primary Examiner* — Yogesh Patel
(74) *Attorney, Agent, or Firm* — Scully, Scott, Murphy & Presser, P.C.

(57) ABSTRACT

A connection arrangement between a dental implant and an abutment is provided. The abutment has a first coronal opening and a second apical opening. The connection arrangement further has a screw and a ring, the ring being suitable for holding a screw inserted in the abutment. The ring is fixed in the first opening of the abutment with a positive fit or a material joint.

24 Claims, 7 Drawing Sheets

(56) References Cited

U.S. PATENT DOCUMENTS

| | | |
|---|---|---|
| 6,743,018 B1 | 6/2004 | Morrow |
| 2001/0053512 A1 | 12/2001 | Nichinonni |
| 2002/0016594 A1* | 2/2002 | Schlapfer et al. ............... 606/73 |
| 2002/0045898 A1* | 4/2002 | Freid et al. ...................... 606/61 |
| 2003/0215769 A1 | 11/2003 | Kim |
| 2003/0224330 A1 | 12/2003 | Aravena et al. |
| 2005/0277928 A1* | 12/2005 | Boschert ......................... 606/61 |
| 2006/0105296 A1* | 5/2006 | Linder et al. .................. 433/173 |
| 2006/0293665 A1* | 12/2006 | Shluzas ........................... 606/61 |
| 2007/0055242 A1* | 3/2007 | Bailly ............................. 606/61 |

FOREIGN PATENT DOCUMENTS

| | | |
|---|---|---|
| EP | 1 362 560 | 11/2003 |
| JP | 07-275267 A | 10/1995 |
| WO | WO 97/14371 A | 4/1997 |
| WO | WO 99/16293 | 4/1999 |
| WO | WO 00/09031 A | 2/2000 |
| WO | WO 00/47113 A | 8/2000 |
| WO | WO 00/62704 A | 10/2000 |
| WO | 01/66033 A1 | 9/2001 |
| WO | WO 2004/032786 A | 4/2004 |

OTHER PUBLICATIONS

Chinese Office Action dated Jun. 8, 2012 for Application/Patent No. 2008801080203 (English language translation only).

Japanese Preliminary Notice of Rejection dated Oct. 8, 2013 issued in corresponding Japanese Patent Application No. 525329/2010.

* cited by examiner

CONNECTION ARRANGEMENT BETWEEN A DENTAL IMPLANT AND AN ABUTMENT

FIELD OF USE OF THE INVENTION

The present invention relates to a connection arrangement between a dental implant and an abutment, in particular for screw- or cylinder-shaped dental implants. Such a connection arrangement comprises a sufficiently known dental implant to be inserted in the jaw bone of a patient and an abutment to be fixed on it. The connection arrangement is inserted in a cylindrical opening in the occlusal part of the dental implant. For the reproducible positioning of the abutment and for securing against rotation, a non-rotationally symmetrical receiving contour can be provided in the receiving bore, a corresponding non-rotationally symmetrical external contour thereto being present on the root portion of the abutment. A female thread extends in the interior of a dental implant which, by screwing in of a screw axially held in an abutment, also called base screw, into the female thread of the dental implant fixes them to each other. After the screwing connection with the dental implant, a conical shaft portion of the screw engages with a positive fit the inner surface of the abutment's apical portion. The shaft portion extends out of the abutment and the threaded shaft engages the thread of the dental implant. The screw thus secures the abutment axially to the dental implant and the non-rotationally symmetrical contour is used as a means for securing against rotation.

STATE OF THE ART

From WO 99/16293, a connection arrangement between a dental implant and an abutment having a screw therein which is held by a bearing ring is known, the bearing ring being secured with a positive (form) fit and a non-positive (force) fit in a supporting area at the apical end of the abutment. Also, the use of a clamped bearing ring provided with slots and/or an abutment also slotted in the apical area would be conceivable.

The preassembled screw is inserted into a bore in the abutment from below and secured by the bearing ring against falling out of the abutment. In addition, it is necessary to secure the bearing ring in the supporting area of the abutment such that partial or complete breaking of the bearing ring in case of high load is prevented. In practice, it has been shown that the screw preassembled in this manner can be detached from the abutment under very high load and that the firm connection of the dental implant with the abutment will no longer be guaranteed. This can be caused by material fatigue since the connection arrangement is subjected to high tensile stresses. A first tensile stress is produced during assembly of the connection arrangement with the dental implant, this tensile stress being produced in the area of the screw seat. When a dental assembly, e.g. a crown or a bridge, is inserted, a second tensile stress is produced by screwing in of the occlusal screw in the abutment thread. The load exerted on the bearing ring forming the screw seat is the sum of the first and the second tensile stress, with the first tensile stress being generally greater than the second tensile stress. This exertion of force in the transition area from the bearing ring and the screw head supported by it can then lead to material fatigue and/or to a breakage of the bearing ring.

It is therefore the object of the present invention to find a solution that withstands greater tensile stresses in the supporting area of the base screw, has a longer service life, has extremely high mechanical strength and can be manufactured without increased costs.

Within the framework of the above object of the invention, another object is the provision of a bearing ring the tensile stress on which is reduced and the risk of breaking of the same is minimized.

SUMMARY OF THE INVENTION

According to one aspect of the present invention, a connection arrangement is provided, which achieves the above-mentioned objects.

In the abutment, there is a first opening formed axially. A screw is then inserted through this first opening in the interior of an abutment. A second opening in the abutment is used for the passage of the screw shaft and of the threaded shaft, where the second opening has a smaller diameter than the first opening and a conical portion. The smaller diameter of the second opening prevents the inserted screw from sliding out of the abutment, with the screw shaft having a portion which is shaped conically and abuts against a corresponding conical interior surface of the abutment. Then a ring is inserted in the coronal area of the abutment and fixed into place. Fixation can be non-positive, positive or by material joint. Pressing in of the ring into the first opening of the abutment has proven particularly advantageous. To fix the ring inside the abutment, good results can also be achieved by snapping-in, screwing, crimping, rolling and welding. Furthermore, especially in case of a snap-in connection, the ring can either be provided with a vertical slot or with one or more expansion slots so that it can be plastically deformed during insertion and, after being released, positively engages the interior surface of the abutment. To increase the pressing effect, the exterior surface of the ring can also be provided with a rough structure so that when the ring is pressed in, a larger surface can be keyed on the interior surface of the coronal abutment opening. Alternatively, the surface of the abutment or both surfaces, the one of the ring and the corresponding surface of the abutment, can also advantageously be roughened. Alternatively, the ring can be provided with a male thread screwed together with a corresponding thread in the first opening.

The ring is manufactured such that it can be inserted in the abutment opening from both sides; in this way the production is simplified, and the insertion direction does not have to be taken into account during assembly. In another embodiment, the upper abutment rim is formed, e.g. by means of crimping, to additionally fix the ring into place in the abutment; instead of crimping, the rim can also be rolled. In another embodiment, the ring can also be fixed in the abutment by means of a positive snap-fit connection. Here, the ring can either be equipped with a catcher which engages a complementarily formed recess in the abutment opening, or the catcher can be formed in the abutment and the complementary recess in the ring. Furthermore, the ring can also be welded together with the abutment in the opening by material joint. Laser welding and ultrasonic welding have proven particularly advantageous for this purpose. These welding procedures are characterized by high welding speed, production of a narrow and slender weld and little thermal distortion, which meets the high precision requirements in dental technology.

In a particular embodiment, the ring both has a female thread and a male thread so that the ring has to be screwed into the opening of the abutment for insertion. The assembling of the connection arrangement, comprised of the abutment with the screw enclosed therein, which cannot fall out due to the coronally arranged ring, and the dental implant takes place as follows. The abutment is introduced in the opening of the dental implant with the threaded shaft of the screw so that the threaded shaft extends into the area of the opening of the dental implant. The exterior surface of the abutment is provided with contours which are used to secure it against rotation. On assembly, these contours engage a complementary structure on the crown assembly as well as a complementary structure on the dental implant. In a central interior portion of the abutment, a cavity is formed which allows a certain play of the screw. The play is determined by the lower edge of the ring and the fit of the conical screw portion and advantageously allows screwing of the screw into a dental implant without tilting. After insertion of the connection arrangement through the axial opening, the screw is screwed into the dental implant with a special screwdriver. The abutment is increasingly drawn into the dental implant until the conically shaped screw shaft is pressed onto the lower interior abutment surface facing the dental implant so that a contact surface is produced which receives the forces occurring from tensile stress of the screw and the dental implant.

SHORT DESCRIPTION OF THE FIGURES

Further features and advantages of the present invention as well as the functioning of the exemplary embodiment of the present invention are described below with reference to the accompanying drawings. The accompanying drawings illustrate the present invention and are furthermore used, together with the description, to exemplify the basics of the invention and to enable a person skilled in the relevant art to manufacture and use the invention.

The following applies throughout the further specification. If reference numbers are included in a figure for the purpose of clarity but not explained in the specification text directly related to it, they are referred to in preceding figure descriptions.

For the sake of clear representation, there is generally no repeated explanation of components in successive figures as long as they can be clearly recognized as "repetitive" components.

Therein:

FIG. 3A shows a lateral partial sectional view of the section line A-A of FIG. 3B;

FIG. 4A shows a lateral partial sectional view of the section line A-A of FIG. 4B;

FIG. 6C shows a lateral partial sectional view of the section line B-B of FIG. 6B;

DESCRIPTION OF PREFERRED EMBODIMENTS OF THE INVENTION

Based on the following FIGS. 1A through 7C, currently preferred embodiments of the present invention of a connection arrangement between a dental implant and an abutment, having an abutment provided with a first and a second opening, a screw and a ring, the ring being suitable to hold a screw inserted in the abutment, will be described.

Figures 1A, 1B, 1C:
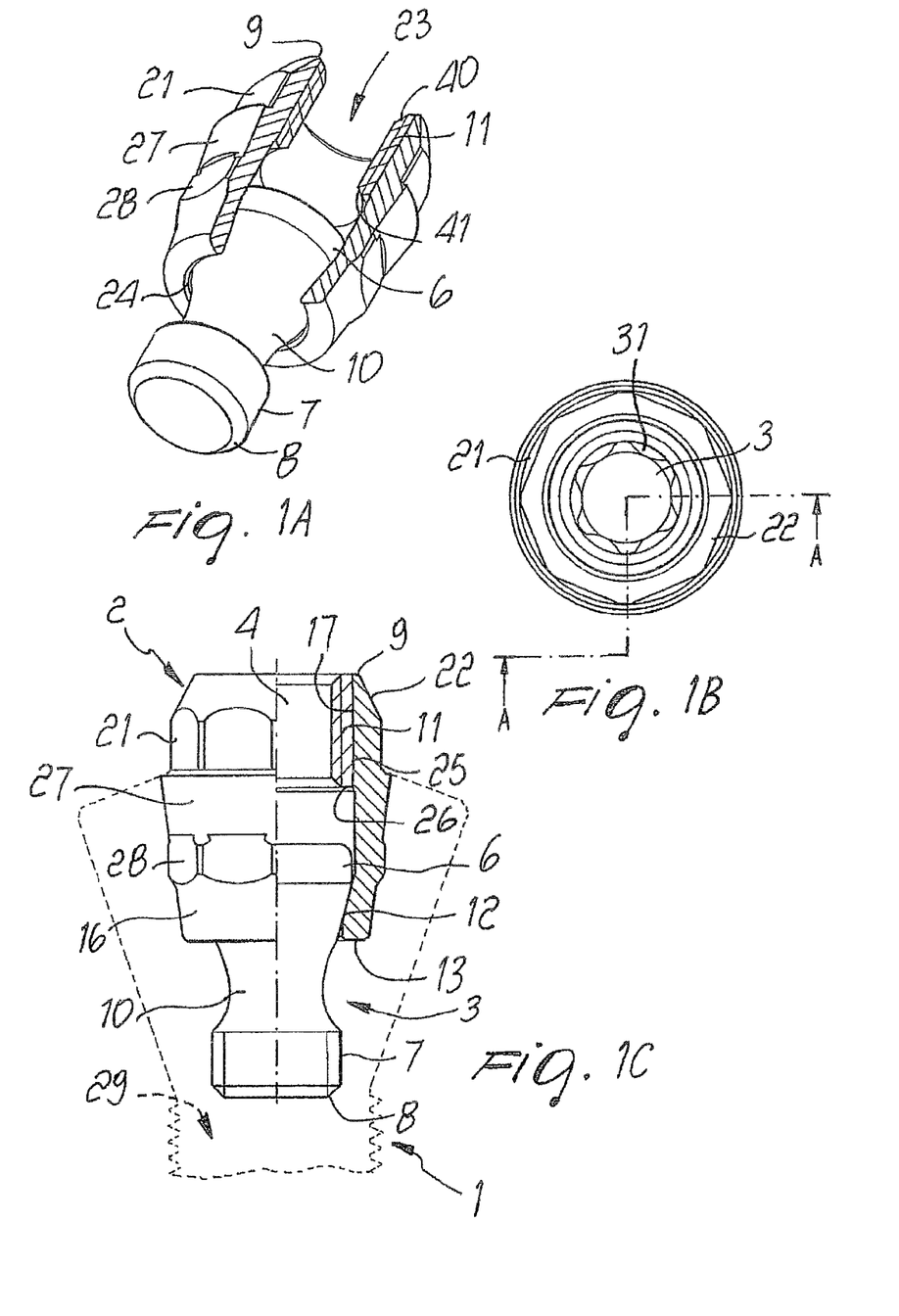
FIG. 1A shows a perspective view of a connection arrangement between a dental implant and an abutment according to a first embodiment of the invention.
FIG. 1B shows a top view of a connection arrangement between a dental implant and an abutment according to FIG. 1A.
FIG. 1C shows a lateral partial sectional view of the section line A-A of FIG. 1B.

FIGS. 1A-1C show a connection arrangement between a dental implant 1 and an abutment 2, with a screw 3 (also called base screw) held within the abutment 2 in different views according to a first embodiment of the invention.

The screw 3 is inserted from above, i.e. through a first opening 23, axially through the abutment 2. The screw shaft 10 of the screw 3 with the adjacent threaded shaft protrudes through a second opening 24 in the abutment 2. The abutment 2 has, starting coronally, an abutment rim 9 which transitions to a cone section 22. Adjacent to it there is a first outer octagon 21 which can be brought into engagement with a supraconstruction or crown (not shown). In its central region, the abutment 2 coronally has a first conical portion 27 and apically a second outer octagon 28 which transitions to an apical end portion 16 of the abutment 2 which is conical as well. For better understanding, FIG. 1C schematically shows a dental implant 1 attached axially on the abutment 2. Inside the abutment 2, there is a ring 4 inserted through the first opening 23 which extends from the abutment rim 9 to a circumferential groove 26 of the abutment 2. The ring can be formed in a well-known manner with an internal thread 11 for receiving dental supraconstructions or crowns. In addition, the ring 4 can preferably be provided with an external thread 15 (in the following also called ring external thread), where in this form the ring is called "ring with a thread", whose method of functioning will be explained in the following.

The ring 4 can either be pressed into the first opening 23 in positive engagement or be fixed into place by means of welding, e.g. laser or ultrasonic welding. If the ring 4 is pressed in, a structure with a thread can also be applied on the ring surface 17 for achieving better adhesion of the ring 4 to an adjacent surface 25 inside the abutment 2. The ring 4 can be fixed coronally above and remote from the screw 3. The adjacent surface 25 forms the transition area between the ring 4 and the abutment 2. If the ring 4 is welded in, the welds are preferably provided in the area of a ring upper edge 40 and/or a ring lower edge 41. At the ring lower edge 41, there is a cavity 5 which is produced if the screw head 6 of the screw 3 does not touch the ring 4, allowing a certain play when the screw 3 is screwed into the dental implant 1. The screw 3 is inserted in the dental implant 1 through a third opening 29 in it, a bevel 8 on the apical end of the screw 3, which is adjacent to the thread 7 of the screw 3, allows easy insertion into a thread (not shown) in the dental implant 1. During this process, the thread 7 of the screw 3 can be screwed to the thread (not shown) of the dental implant 1. At its coronal end, the screw 3 is provided with an engagement contour 31 so that, when the screw 3 is screwed to the dental implant 1 by means of a screwdriver inserted in the engagement contour 31, the conical area forming the screw head above the screw shaft 10 is in positive engagement with a contact surface 12 of the abutment 2 which is substantially limited by an abutment lower edge 13.

Figures 2A, 2B, 2C:
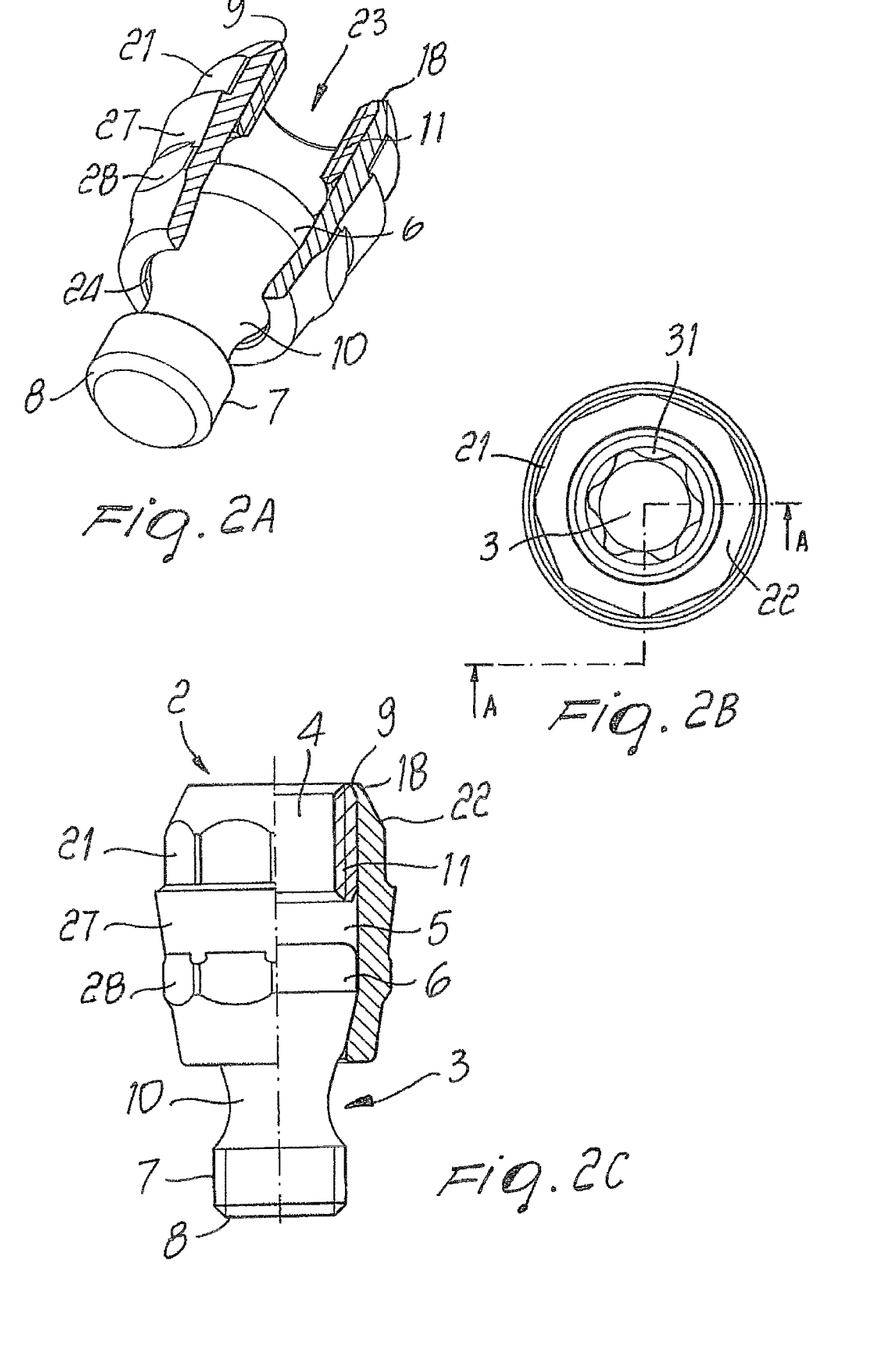
FIG. 2A shows a perspective view of a connection arrangement between a dental implant and an abutment according to a second embodiment of the invention.
FIG. 2B shows a top view of a connection arrangement between a dental implant and an abutment according to FIG. 2A.
FIG. 2C shows a lateral partial sectional view of the section line A-A of FIG. 2B.

FIGS. 2A-2C show a second embodiment of the invention, where in contrast to the first embodiment, the ring 4 inside the abutment 2 is pressed in through the first opening 23 and extends from the abutment rim 9 to the circumferential groove 26. In the transition area between the cone section 22 and the abutment rim 9, the abutment rim 9 is slightly tilted toward the center axis of the abutment 2 by means of crimping 18. Instead of crimping 18, this positive engagement can also be provided by rolling.

Figures 3A, 3B, 3C:
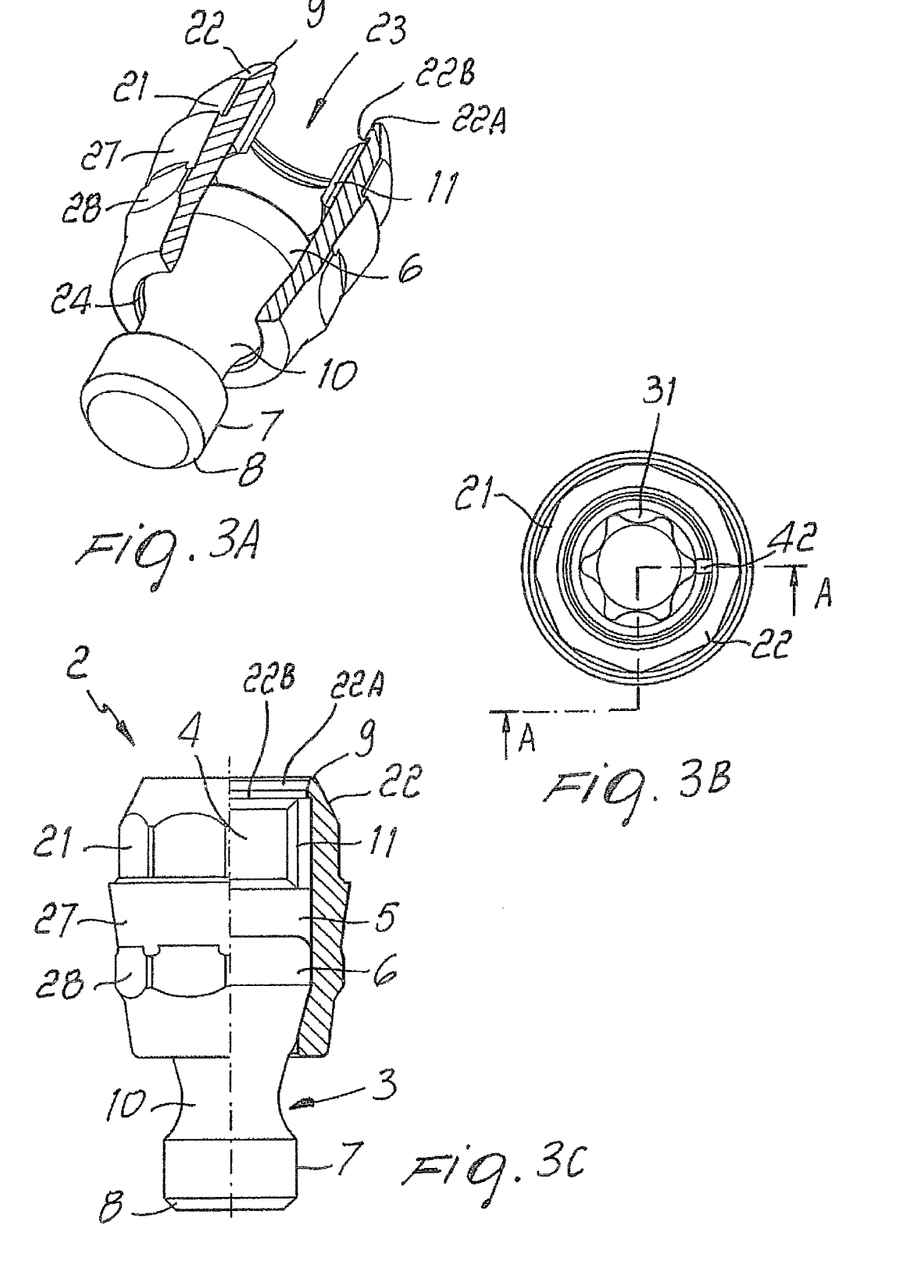
FIG. 3A shows a perspective view of a connection arrangement between a dental implant and an abutment according to a third embodiment of the invention.
FIG. 3B shows a top view of a connection arrangement between a dental implant and an abutment according to FIG. 3A.

FIGS. 3A-3C show a third embodiment of the invention where in contrast to the first embodiment, the ring 4 has a vertical through slot 42. On the abutment rim 9, in the area of the first opening 23, a chamfer 22A is formed which is limited by an abutment catcher 22B. For fixation in the abutment 2, the ring 4 is first compressed so that it has approximately the same diameter as the first opening 23 or slightly smaller in order to fit through the opening 23. The tension built up in the ring 4 by the compression enables the ring 4 to expand after it has passed the abutment catcher 22B in the apical direction and is thus fixed firmly into place on the inner surface of the abutment 2.

Figures 4A, 4B, 4C:
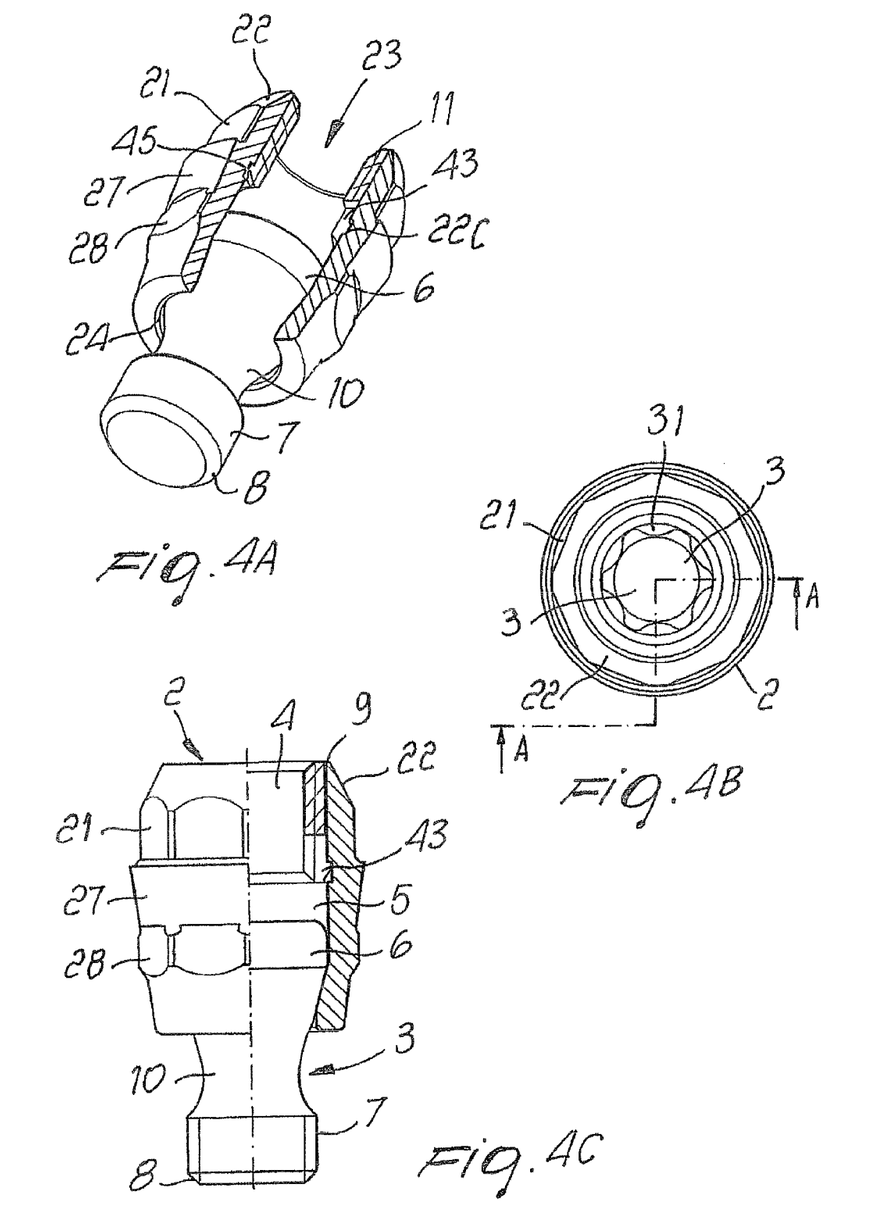
FIG. 4A shows a perspective view of a connection arrangement between a dental implant and an abutment according to a fourth embodiment of the invention.
FIG. 4B shows a top view of a connection arrangement between a dental implant and an abutment according to FIG. 4A.

FIGS. 4A-4C show a fourth embodiment of the invention, where in contrast to the first embodiment, the ring 4 is provided with two or more expansion slots 43. The ring 4 is pressed into the abutment 2 for fixation, whereby the ring 4 yields in the area of the expansion slots 43 and snaps into place with the ring catcher 45 in an abutment recess 22C as it has reached the abutment recess 22C located in the first opening 23.

Figures 5A, 5B, 5C:
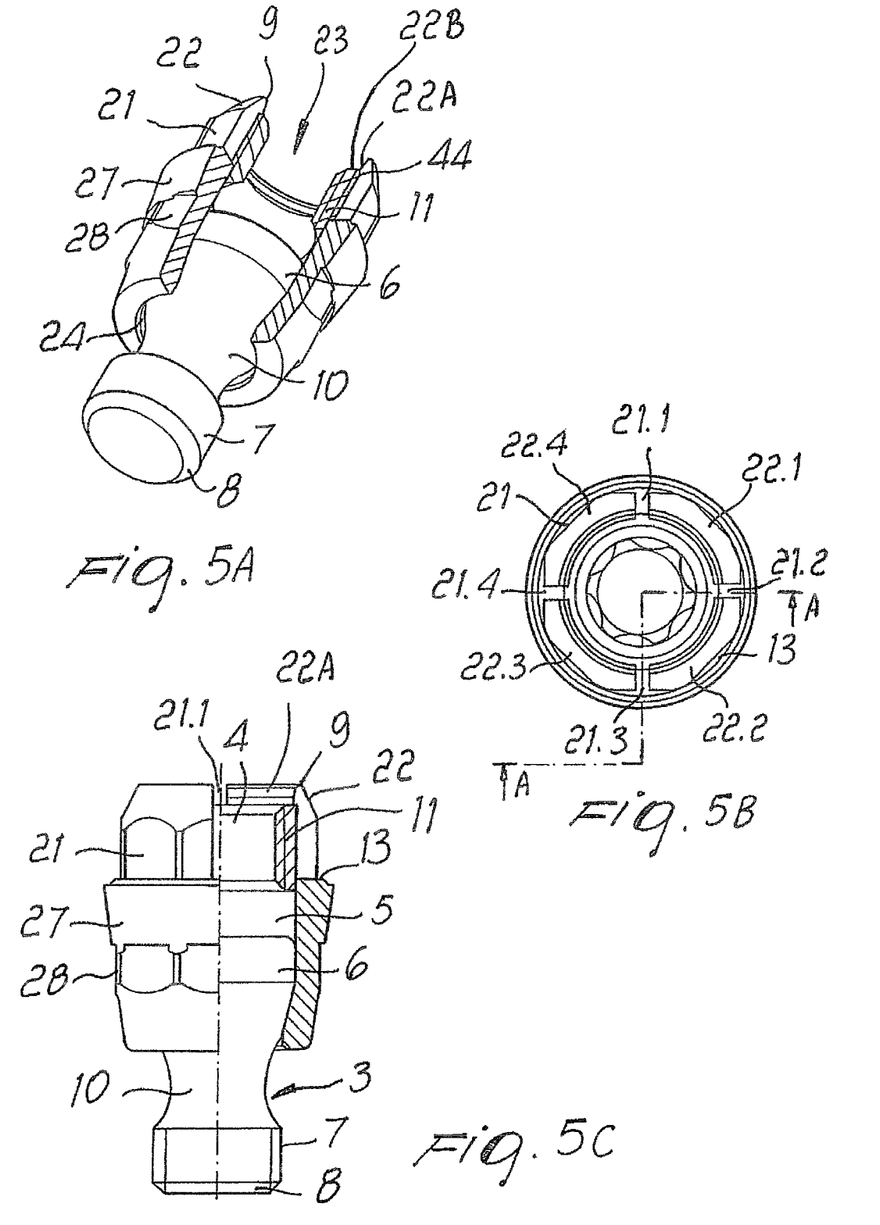
FIG. 5C shows a perspective view of a connection arrangement between a dental implant and an abutment according to a fifth embodiment of the invention.
FIG. 5B shows a top view of a connection arrangement between a dental implant and an abutment according to FIG. 5A.
FIG. 5A shows a lateral partial sectional view of the section line A-A of FIG. 5B.

FIGS. 5A-5C show a fifth embodiment of the invention, where similar to the first embodiment, the ring 4 is embodied as a continuous ring. In contrast to the first embodiment, however, the coronal abutment portion formed by the cone section 22 and the first outer octagon 21 is provided with several symmetrically arranged expansion slots 21.1, 21.2, 21.3, 21.4. In this manner, the coronal abutment portion is divided into several symmetrically arranged segments 22.1, 22.2, 22.3, 22.4. The ring 4 is pressed into the abutment 2 for fixation, which causes the symmetrically arranged segments 22.1, 22.2, 22.3, 22.4 and the ring 4 to expand up to the point where the entire ring 4 with the ring recess has passed the abutment catcher 22B. At this point, the previously expanded segments 22.1, 22.2, 22.3, 22.4 again become narrow and fix the ring 4 in the abutment 2. For easy insertion of the ring 4, there is a chamfer 22A between the abutment rim 9 and the abutment catcher 22B. It is also possible to combine the embodiment in FIGS. 5A-5C with a vertical slot of the embodiment in FIGS. 3A-3C or FIG. 7.

Figures 6A, 6B, 6C:
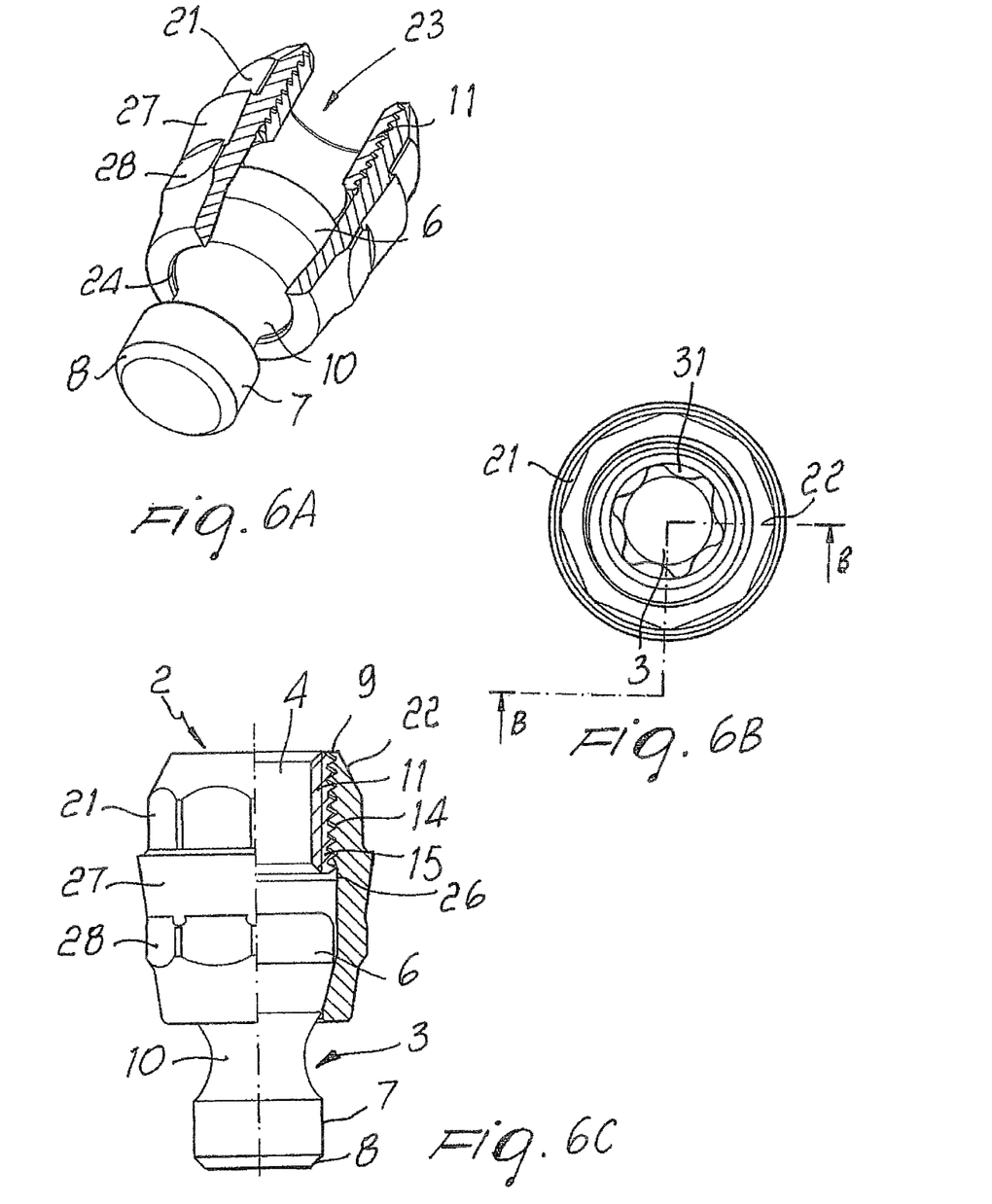
FIG. 6C shows a perspective view of a connection arrangement between a dental implant and an abutment according to a sixth embodiment of the invention.
FIG. 6B shows a top view of a connection arrangement between a dental implant and an abutment according to FIG. 6A.

FIGS. 6A-6C show a sixth embodiment of the invention, where similar to the first embodiment, the ring 4 is embodied as a continuous ring 4. The ring 4 has a female thread 11 and a ring male thread 15. The first opening 23 of the abutment 2 has an abutment female thread 14 starting from the abutment rim 9 down to a circumferential groove 26 provided centrally in the interior of the abutment 2. The ring 4 is screwed in positive engagement into the abutment female thread 14, with the circumferential groove 26 preventing overtwisting of the ring 4 in the apical direction. Advantageously, the female thread 11 and the ring male thread 15 act in the same direction.

Figure 7A:
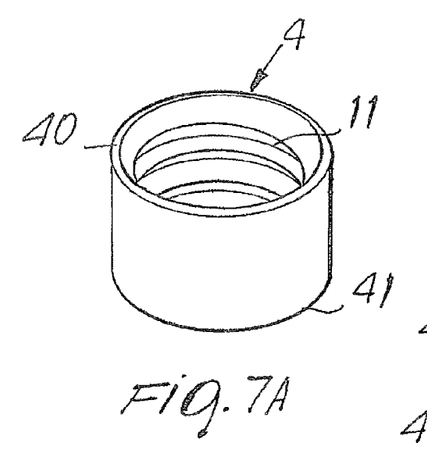
FIG. 7A shows a perspective view of a ring in a closed embodiment.

FIG. 7A shows a full version of a ring 4. In this embodiment, the ring 4 consists of a tube-shaped element whose upper edge 40 forms a thread shoulder for the female thread 11. On the lower ring edge (41), there is the complementary thread shoulder of the female thread 11. The female thread 11 is formed on the entire inner surface of the ring 4. The exterior ring surface can be smooth or structured for preventing release during screwing. The structure can have the form of grooves, knurling, thread or micro-thread, other roughness structures being possible as well.

Figure 7B:
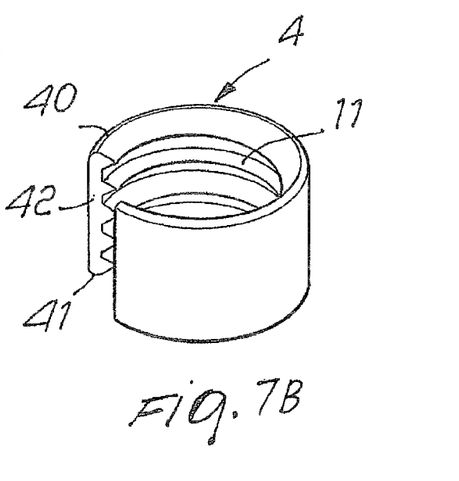
FIG. 7B shows a perspective view of a ring with a vertical slot.

FIG. 7B shows a ring 4 which has a vertical through slot 42 so that it is open in this portion. The ring 4 is also a tube-shaped element with the female thread 11 being formed on the entire interior surface.

Figure 7C:
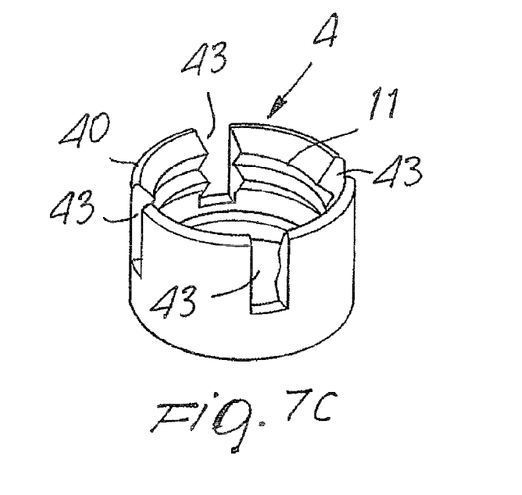
FIG. 7C shows a perspective view of a ring with several expansion slots.

FIG. 7C shows a full version of a ring 4 with several expansion slots 43, the expansion slots 43 being arranged symmetrically and extending to the central portion of the ring.

Figure 7D:
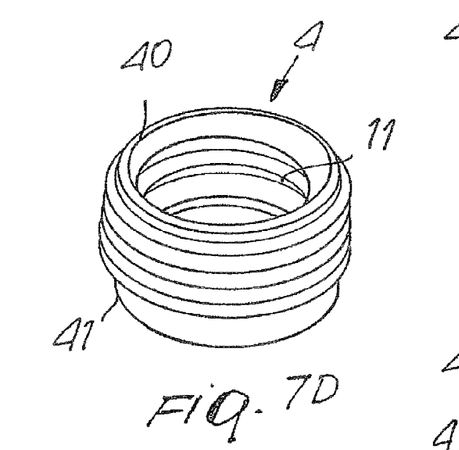
FIG. 7D shows a perspective view of a ring with a male and a female thread.

FIG. 7D shows a full version of a ring 4 with a female thread 11 formed on the entire surface and a ring male thread 15.

LIST OF REFERENCE NUMBERS 1. dental implant
2. abutment
3. screw or base screw, respectively
4. ring
5. cavity
6. screw head
7. threaded shaft
8. bevel
9. abutment rim
10. screw shaft
11. internal thread of the ring
12. contact surface
13. lower abutment edge
14. abutment female thread
15. ring external thread
16. apical end portion
17. ring surface
18. crimping
19.
20.
21. $1^{st}$ outer octagon
21.1 $1^{st}$ expansion slot
21.2 $2^{nd}$ expansion slot
21.3 $3^{rd}$ expansion slot
21.4 $4^{th}$ expansion slot
22. cone section 22A chamfer
22B abutment catcher
22C abutment recess
22.1 $1^{st}$ segment
22.2 $2^{nd}$ segment
22.3 $3^{rd}$ segment
22.4 $4^{th}$ segment
23. $1^{st}$ opening
24. $2^{nd}$ opening
25. adjacent surface of the abutment
26. circumferential groove
27. $1^{st}$ conical portion
28. $2^{nd}$ outer octagon
29. $3^{rd}$ opening
30.
31. engagement contour
32. $2^{nd}$ conical portion
33.
34.
35.
36.
37.
38.
39.
40. upper ring edge
41. lower ring edge
42. vertical slot
43. expansion slots
44.
45. ring catcher

The invention claimed is:

1. A dental implant connection arrangement, comprising:
a screw,
an abutment provided with a first coronal opening and a second apical opening, the first coronal opening being sized to allow insertion of the screw through the first coronal opening into the interior of the abutment, and
a circular ring, wherein the ring retains the screw inserted in the abutment,
wherein the ring is fixed fully within the first coronal opening of the abutment after insertion of the screw, at a location coronally above and remote from the screw with a non-positive or a positive fit or a material joint, such that a cavity is formed in the interior of the abutment, which allows play of the screw prior to attachment to a dental implant.

2. The connection arrangement according to claim 1, wherein a shaft of the screw has a portion which is shaped conically and abuts against a corresponding conical interior surface of the abutment.

3. The connection arrangement according to claim 1, wherein the ring is pressed into the first coronal opening of the abutment with a positive fit.

4. The connection arrangement according to claim 3, wherein the abutment has a coronally positioned abutment rim which is formed.

5. The connection arrangement according to claim 4, wherein forming of the abutment rim is carried out by crimping.

6. The connection arrangement according to claim 4, wherein forming of the abutment rim is carried out by rolling.

7. The connection arrangement according to claim 4, wherein forming of the abutment rim is carried out by crimping and/or rolling.

8. The connection arrangement according to claim 3, wherein the ring is provided with a vertical slot.

9. The connection arrangement according to claim 3, wherein the ring is provided with two or more expansion slots.

10. The connection arrangement according to claim 3, wherein the abutment is coronally provided with one or more expansion slots.

11. The connection arrangement according to claim 1, wherein the ring has a male thread which is screwed into the first coronal opening of the abutment with a positive fit.

12. The connection arrangement according to claim 1, wherein the ring is fixed in the first coronal opening of the abutment with a positive snap-fit.

13. The connection arrangement according to claim 12, wherein the snap-in connection is provided by a catcher in the abutment.

14. The connection arrangement according to claim 12, wherein the snap-in connection is provided by an abutment recess in the abutment and a ring catcher in the ring.

15. The connection arrangement according to claim 12, wherein the ring is provided with a vertical slot.

16. The connection arrangement according to claim 12, wherein the ring is provided with two or more expansion slots.

17. The connection arrangement according to claim 12, wherein the abutment is coronally provided with one or more expansion slots.

18. The connection arrangement according to claim 1, wherein the ring is welded by material joint in the first coronal opening of the abutment.

19. The connection arrangement according to claim 18, wherein the ring is welded to the abutment by laser welding or ultrasonic welding.

20. The connection arrangement according to claim 1, wherein a ring surface of the ring and/or the adjacent surface of the abutment at the first coronal opening of the abutment is provided with a structure.

21. The connection arrangement according to claim 20, wherein the structure is embodied in the form of grooves, knurling, thread or micro-thread.

22. The connection arrangement according to claim 1, wherein the ring is fixed coronally above and remote from the screw and wherein a shaft of the screw has a portion which is shaped conically and abuts against a corresponding conical interior surface of the abutment.

23. The connection arrangement according to claim 1, wherein the ring is fixed within the first coronal opening, such that the ring is fully housed within the abutment.

24. The connection arrangement according to claim 1, wherein the ring is fixed in the first coronal opening prior to connection of the abutment to the implant, such that the screw is preassembled within the abutment.

* * * * *